(12) United States Patent
Senac

(10) Patent No.: US 8,436,991 B2
(45) Date of Patent: May 7, 2013

(54) DEVICE FOR ANALYSING MATERIALS BY PLASMA SPECTROSCOPY

(75) Inventor: Stéphane Senac, Greasque (FR)

(73) Assignee: Bertin Technologies, Montigny le Bretonneux (FR)

( * ) Notice: Subject to any disclaimer, the term of this patent is extended or adjusted under 35 U.S.C. 154(b) by 109 days.

(21) Appl. No.: 13/131,461

(22) PCT Filed: Nov. 3, 2009

(86) PCT No.: PCT/FR2009/001272
§ 371 (c)(1),
(2), (4) Date: Jul. 29, 2011

(87) PCT Pub. No.: WO2010/061069
PCT Pub. Date: Jun. 3, 2010

(65) Prior Publication Data
US 2012/0044488 A1  Feb. 23, 2012

(30) Foreign Application Priority Data
Nov. 28, 2008 (FR) ...................................... 08 06712

(51) Int. Cl.
*G01J 3/30* (2006.01)
(52) U.S. Cl.
USPC .......................................................... 356/316

(58) Field of Classification Search .................... None
See application file for complete search history.

(56) References Cited

U.S. PATENT DOCUMENTS
7,394,537 B1 * 7/2008 Lindfors et al. .............. 356/318
2005/0229698 A1 10/2005 Beecroft et al.

OTHER PUBLICATIONS
International Search Report and Written Opinion for International Application No. PCT/FR2009/001272, mailed Jan. 5, 2010.
Fichet, P., et al; "Determination of Impurities in Uranium and Plutonium Dioxides by Laser-Induced Breakdown Spectroscopy"; Applied Spectroscopy; 1999; vol. 53; Issue 9, pp. 1111-1117.

* cited by examiner

*Primary Examiner* — Tarifur Chowdhury
*Assistant Examiner* — Abdullahi Nur
(74) *Attorney, Agent, or Firm* — Alston & Bird LLP

(57) ABSTRACT

A device for analyzing materials by plasma spectroscopy is of the portable and independent type, comprising a housing (10) containing a laser generator (18) that emits laser pulses that are focused on the surface of a material to be analyzed by means of a parabolic mirror (32) that is movable in translation inside the housing in order to perform a series of spot measurements along a scan line on the surface of the material to be analyzed and in order to take a measurement from a calibration sample (50) mounted in the measurement endpiece (22) of the housing (10).

19 Claims, 4 Drawing Sheets

DEVICE FOR ANALYSING MATERIALS BY PLASMA SPECTROSCOPY

FIELD OF THE INVENTION

The invention relates to a device for analyzing materials by plasma spectroscopy.

BACKGROUND

Determining or verifying the chemical compositions of various materials and articles, in particular because of the increasing complexity of the materials that are used in industry and because of a desire to be environmentally friendly (recycling, health inspections, . . . ), has led to inspection and measurement techniques being developed that are usable on site and in real time and that avoid taking away samples and sending the samples to analysis laboratories.

The techniques that are presently available comprise spark spectroscopy, X-ray fluorescence spectroscopy, and laser-induced plasma spectroscopy.

In summary, spark spectroscopy devices, which generate a plasma by means of an electric arc between the material to be analyzed and an anode through which an electric pulse is caused to pass, suffer from the essential drawbacks of not being portable, of requiring samples of the materials to be prepared, of operating only with materials that conduct electricity, and of requiring contact with the material being analyzed, thus making the use of that technique difficult or even impossible on moving articles, articles at high temperature, or articles located in an environment that is contaminated, difficult, or dangerous.

X-ray fluorescence devices are portable, but they are suitable for measuring only those elements that are lighter than silicon. They need to be put into contact with the materials of the articles to be analyzed and they are the subject of safety constraints and regulations.

In practice, they do not enable measurements to be made on grades of aluminum that differ from one another in terms of silicon or magnesium, or on steels for which it is necessary to measure carbon content, or on organic compounds based on carbon, hydrogen, nitrogen, and oxygen.

Existing laser-induced plasma spectroscopy devices, also known as laser-induced breakdown spectroscopy (LIBS) devices, are essentially laboratory appliances that are perhaps transportable, but that are never portable and self-contained, essentially because they use laboratory laser generators that are large in size and bulky, and because they involve a series of spectrometers for analyzing the spectral components of the plasma in various wavelength ranges. Incorporating a plurality of spectrometers in such appliances increases their cost and their weight. In addition, the useful signal received by each spectrometer is no more than a fraction of the useful signal emitted by the plasma, thereby degrading the photometric balance and harming measurement sensitivity.

Furthermore, in those known plasma spectroscopy devices, the laser generator is often connected to a measurement probe by an optical fiber, which means that it is not possible to convey high levels of laser energy at wavelengths shorter than 532 nanometers (nm) and that it is not possible to take measurements on plastics materials or on organic compounds for which it is preferable to use an ultraviolet laser beam having a wavelength of 266 nm. Furthermore, the optical fiber degrades the radiance of the laser beam (where radiance is its energy divided by the product of the emission area and the emission solid angle), such that it is more difficult to focus the beam on the material or the article to be analyzed and it becomes necessary to take measurements in contact with the article or to increase the size of the optical components used, thereby giving rise to an increase in their bulk and their cost.

SUMMARY

A particular object of the present invention is to provide a solution to these problems that is simple, effective, and inexpensive.

The invention provides a laser-induced plasma spectroscopy device (or LIBS device) that is portable and independent, that is highly sensitive and very accurate and that can be used with any type of material, whether on site or in line on a system for processing materials or articles.

To this end, the invention provides a device for analyzing materials by plasma spectroscopy, the device comprising a laser generator, laser pulse focusing means for focusing laser pulses produced by the generator onto a material to be analyzed, plasma light pick-up means for picking up light from the plasma produced by the laser pulses at the surface of the material, and transmission means for transmitting said light to a spectrometer associated with photodetectors having outputs connected to data processor means, the device being characterized in that the laser pulse focusing means and the plasma light pick-up means are constituted by an optical system mounted with the laser generator and laser generator control cards in a housing that is portable and suitable for handling in one hand, the optical system being mounted in the housing between the laser generator and an outlet window and comprising a first parabolic mirror for focusing the laser beam on the material to be analyzed and for picking up the light from the plasma, and two plane mirrors arranged relative to the first parabolic mirror to reflect to said mirror the laser pulses emitted by the generator and to reflect the light from the plasma as received from the first parabolic mirror to a second parabolic mirror that focuses said light on one end of the transmission means connected to the spectrometer.

This configuration presents certain advantages:
the pulses produced by the laser generator are not transmitted by an optical fiber;
the optical system with two parabolic mirrors is very compact and serves both to transit laser pulses and to focus them on the surface of the material or the article to be analyzed, and also to transmit light from the plasma and focus it on the means connected to the analysis spectrometer; and
the device is usable on a production line.

Advantageously, the first parabolic mirror has a reflection zone for laser pulses and a reflection zone for light that has been picked up, these two zones being adjacent and separate from each other and including reflective coatings that are adapted to the wavelengths they have to reflect.

According to another characteristic of the invention, the first parabolic mirror is movable along the axis of incidence of the laser pulses so as to scan in translation the surface of the material to be analyzed.

Advantageously, the first parabolic mirror is mounted on a motor-driven support that is controlled by the control means of the laser generator.

This makes it possible to scan the surface of the material that is to be analyzed along a certain length and to make a certain number of measurements automatically at different points along the line scanned on the surface of the material. Thereafter, by processing the signals that are picked up, it is possible to filter out erroneous measurements that are due to impurities or to spot defects in composition and to make use of an average of the spectral of the various measurements taken in order to carry out the analysis. It is thus possible to be insensitive to local non-uniformities in materials, so it is possible to take measurements on materials that are slightly heterogeneous, and the repeatability and the accuracy of the measurements are improved.

According to another characteristic of the invention, a measurement endpiece mounted on the housing in register with the outlet window includes a calibration mirror associated with a calibration sample that is also mounted in the endpiece in such a manner that when the first parabolic mirror reaches one end of its stroke, the laser pulses deflected by the parabolic mirror encounter the calibration mirror and are directed onto the calibration sample.

These calibration means make it possible to correct potential spectrum drift of the spectrometer that result from temperature, and to correct and verify the calibration curves that are used for determining the concentrations of the ingredients of the analyzed materials.

A calibration fitting may also be provided that can be mounted on the measurement endpiece or that may take the place of the measurement endpiece, the fitting including a motor-driven support carrying some number of samples of different materials that are designed to be placed one after another on the axis of laser pulses at the outlet from the device.

This makes it possible, optionally at regular intervals, to calibrate the device automatically as a function of the type of analyses to be carried out, particularly when the looked-for accuracy of analysis is at a maximum.

For example, it is possible to use different calibration fittings in order to carry out measurements on different materials (e.g. aluminum, steel, a plastics material, etc. . . . ).

According to another characteristic of the invention, the spectrometer of the device comprises a housing formed with an inlet slot fitted with a connector for coupling to an optical fiber that conveys the light from the plasma, a diffraction grating arranged in alignment with the slot, a mirror receiving the light from the grating, and at least one linear detector with photodetectors that receive the light reflected by the mirror.

Advantageously, the spectrometer has at least two substantially juxtaposed linear detectors covering distinct ranges of the light spectrum, e.g. 200 nanometers (nm) to 240 nm and 300 nm to 340 nm, depending on the types of material to be analyzed.

Mounting a single spectrometer in the device of the invention is inexpensive and effective since it avoids sharing the light flux picked up by the device over a plurality of spectrometers.

The use of a plurality of linear detectors enables very accurate measurements to be taken over a plurality of wavelength ranges.

According to another characteristic of the invention, the device also includes means for injecting an inert gas into the plasma formation zone at the surface of the material to be analyzed, said means being easily removable and replaceable and comprising an inert gas cartridge carried by the housing and fitted with an outlet solenoid valve that is connected by a pipe to the measurement endpiece.

This makes it possible to improve measurement accuracy and to perform in situ measurements on atoms that are normally present in air, such as nitrogen, carbon, hydrogen, and oxygen.

The device of the invention may also include means for heating the plasma produced at the surface of the material, these heater means advantageously comprising a laser diode emitting a light beam that is focused by the first parabolic mirror onto the plasma.

Heating the plasma serves to increase the level of the signal and the sensitivity of the measurement. It is known in the art to perform such heating by using two laser pulses ("a double pulse") so as to increase the lifetime of the plasma, reduce measurement noise, and increase the stability of the plasma. Nevertheless, producing a double pulse requires the laser generator to be adapted, and the energy in each pulse is halved. It is therefore more advantageous to use a laser diode that can be controlled in power, in energy, and in operating rates. A large amount of energy is thus made available and the plasma may be heated remotely.

In a first embodiment, the above-mentioned portable housing containing the laser generator may be connected to another unit containing the spectrometer, and also containing electrical power supply means, e.g. of the battery type, and a control and computer processor card.

In this embodiment, the weight of the housing containing the laser generator is about 2 kilograms (kg) while the weight of the unit is about 3 kg to 4 kg.

In another embodiment, the spectrometer, the electrical power supply means, e.g. of the battery type, and the control and processor card are fitted on and secured to the housing containing the laser generator.

A single appliance is then made available that is portable and completely independent, weighing about 3.5 kg.

According to another characteristic of the invention, the device may also be used on a production line. It is then advantageously fitted with a system for scanning or deflecting the light beam and it is typically situated at a distance of 10 centimeters (cm) to 100 cm from the products that are to be inspected.

BRIEF DESCRIPTION OF THE DRAWINGS

The invention can be better understood and other characteristics, details, and advantages thereof appear more clearly on reading the following description made by way of example with reference to the accompanying drawings, in which.

DETAILED DESCRIPTION

Figure 1:
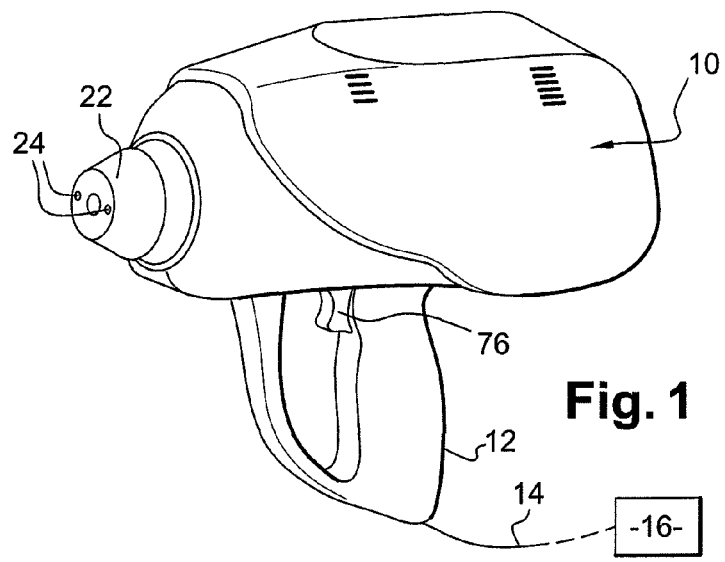
FIG. 1 is a diagrammatic perspective view of a first embodiment of the invention.
Figure 2:
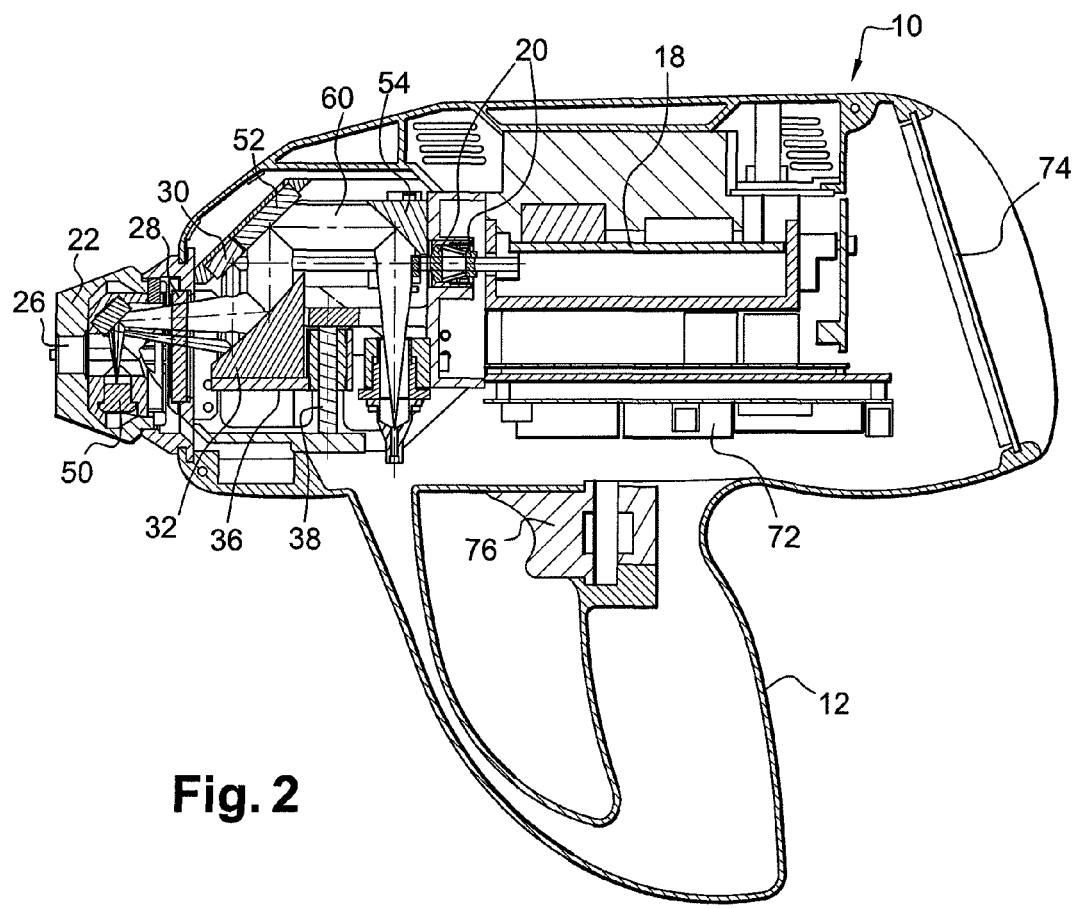
FIG. 2 is a fragmentary diagrammatic view in section of the FIG. 1 appliance.

FIGS. 1 to 5 show a first embodiment of the invention, in which a housing 10 fitted with a handle 12 is connected by a cable 14 to a unit 16 that contains in particular a spectrometer and electrical power supply means, of the battery type.

The housing 10 contains (FIG. 2) a laser generator 18 having its outlet pointing axially towards the front of the housing 10 and it includes two silica lenses 20 through which pulses emitted by the generator 18 pass.

The front end of the housing 10 caries a measurement endpiece 22 for applying against the material or the article that is to be analyzed, with its end including two movable safety contacts 24 enabling the device to operate when they are pushed in to an operating position by pressing the endpiece 22 against the material or the article that is to be analyzed.

The endpiece 22 is tubular and includes an axial orifice 26 for delivering laser pulses and for picking up light.

The front end of the housing 10 on which the endpiece 22 is mounted also includes a window 28, e.g. of cast silica, through which laser pulses are delivered and light is picked up.

Figure 3:
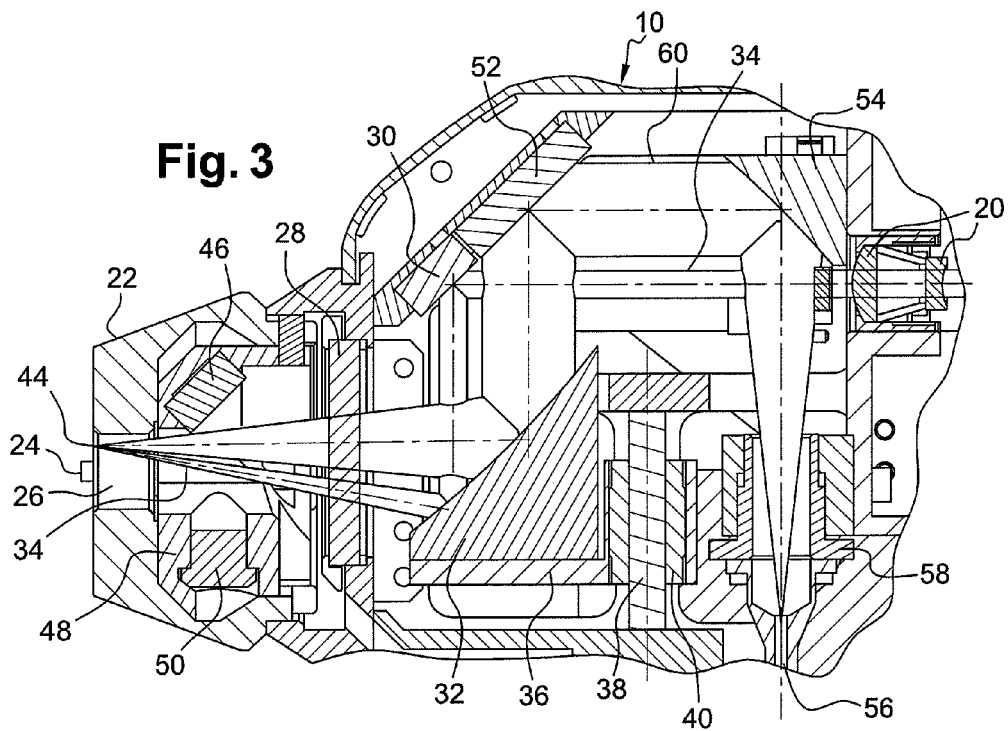
FIGS. 3 and 4 are fragmentary diagrammatic views in section showing the operation of the appliance.

Between the outlet lenses 20 of the laser generator and the window 28, the front portion of the housing 10 contains an optical system for guiding laser pulses and for collecting light, which system essentially comprises a plane mirror 30 inclined at 45° relative to the optical axis of the generator so as to reflect laser pulses vertically downwards onto a first zone of a first parabolic mirror 32, which reflects the laser pulses towards the window 28 and focuses them at the front end of the measurement endpiece 22 that is to be put into contact with the material or the article that is to be analyzed, as shown in FIG. 3 where the path followed by the laser pulses is given reference 34.

The first parabolic mirror 32 is carried by a support 36 that is movable in vertical translation by means of a motor-driven wormscrew system 38 having a nut 40 carried by the support 36 engaged thereon, rotation of the screw 38 serving to move the first parabolic mirror 32 in translation along the axis of incidence of the laser pulses so that the point 44 on which the pulses are focused is scanned through a distance, e.g. of centimeter order, over the surface of the material or the article that is to be analyzed.

Figure 4:
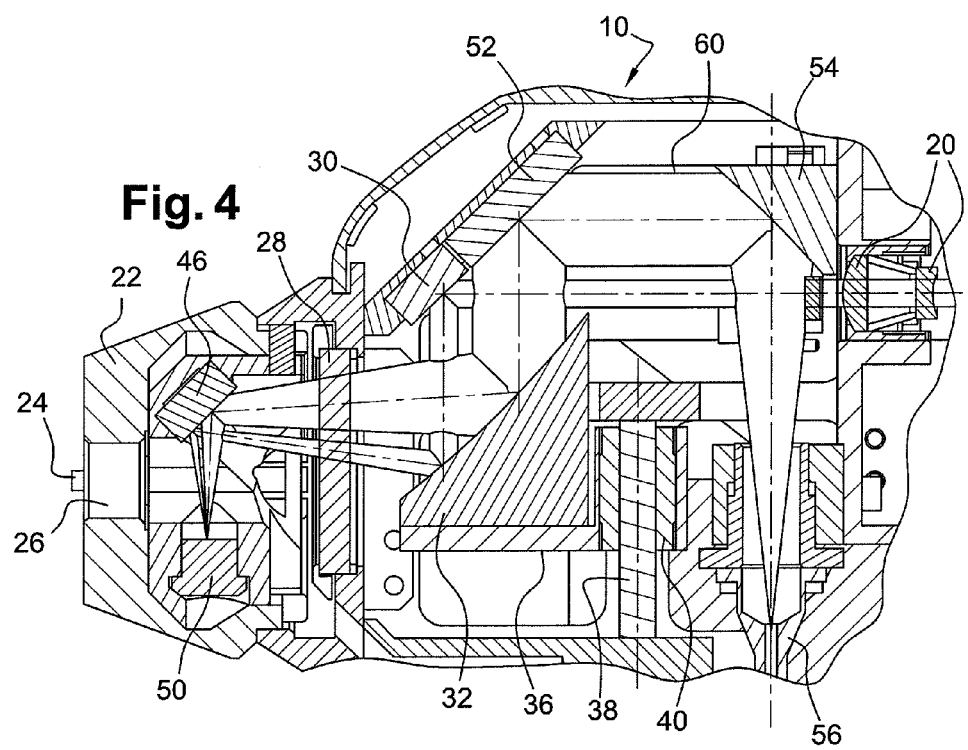

When the first parabolic mirror is at the end of its stroke, e.g. in its top position as shown in FIG. 4, the invention provides for it to send laser pulses onto a plane mirror 46 mounted on the inside surface of the measurement endpiece 22 and orient it in such a manner as to reflect the laser pulses towards a sample 50 carried by a support 48 mounted in stationary manner within the endpiece 22, e.g. in vertical alignment with the mirror 46, as shown in the drawing.

The optical system mounted inside the housing 10 also includes means for picking up the light emitted by the plasma that is generated by the laser pulses focused on the surface of the material or the article that is to be analyzed.

This light is picked up through the window 28 and reflected by a second zone of the first parabolic mirror 32 towards a second plane mirror 52 placed beside the first plane mirror 30 and on the same support, in order to reflect the light that has been picked up towards a second parabolic mirror 54 that focuses the picked-up light on the end of an optical fiber 56 mounted by a connector 58 in an orifice of the housing 10, the optical fiber 56 conveying the picked-up light to a spectrometer mounted in the unit 16. The two plane mirrors 30, 52 are located vertically relative to the first parabolic mirror 32 and horizontally relative to the second parabolic mirror 54.

The second parabolic mirror 54 is off the optical axis of the laser generator 18 and is oriented perpendicularly to the first parabolic mirror 32.

The path of the light that is picked up is given reference 60 in the drawings, where it can be seen that the reflection of light on the first parabolic mirror 32, on the second plane mirror, and on the second parabolic mirror 54 takes place at 90°.

Figure 5:
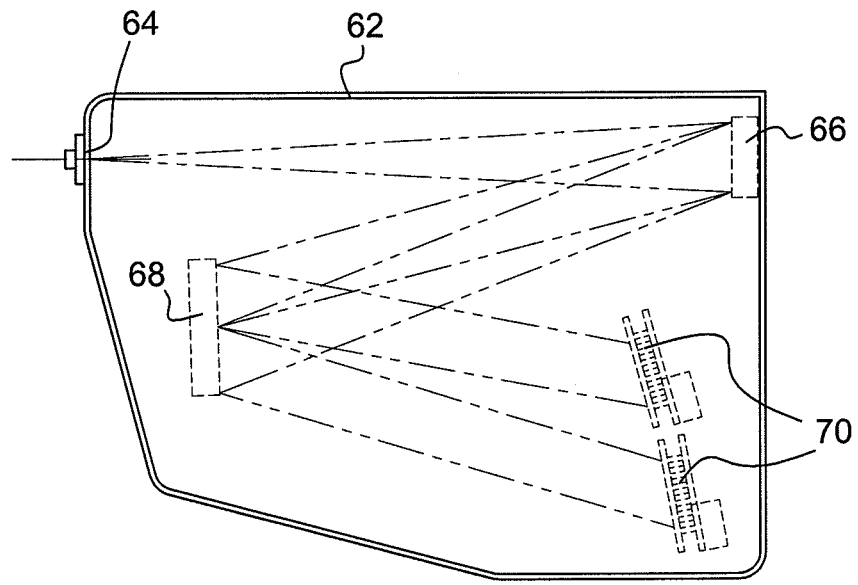
FIG. 5 is a diagram showing the spectrometer of the appliance of the invention.

By way of example, the optical fiber 56 passes through the trigger guard of the handle 12 and goes to the spectrometer that is shown diagrammatically in FIG. 5, which spectrometer essentially comprises, inside a housing 62: an inlet slot 64 aligned with a diffraction grating 66 having a plane mirror 68 mounted to face it and reflect the diffracted light onto two detectors 70 such as two linear strips of charge-coupled device (CCD) type photodetectors or the like, for example, the two detectors 70 being substantially juxtaposed and covering two different ranges of the light spectrum.

In the embodiment shown in the drawings, the laser generator 18 is of the Nd:YAG type that emits infrared radiation at a wavelength of 1064 nm. The laser generator is pumped by light-emitting diodes operating in pulse mode and it is fitted with an electro-optical modulator (a Q switch) operating at 20 hertz (Hz), thus enabling 10 millijoule (mJ) laser pulses to be delivered having a half-height duration of 5 ns at a rate of 20 Hz. The laser beam has a Gaussian intensity profile and its diameter is about 1 millimeter (mm) at the outlet from the generator 18.

If necessary in the intended applications, the frequency of the laser beam may be doubled, tripled, or quadrupled by means of non-linear crystals that are placed on the path of the laser beam in order to change its wavelength from 1064 nm to 532 nm, and then to 266 nm, for example.

The two lenses 20 through which the laser pulses pass at the outlet from the generator 18 are respectively a diverging lens and a converging lens so as to increase the laser beam diameter to about 2.5 mm in order to reduce the power density on the first parabolic mirror 32 and on the plane mirrors 30 and 46, and so as to focus the laser pulses with a smaller diameter on the material or the article to be analyzed.

The first plane mirror 30 that reflects the laser pulses towards the first zone of the first parabolic mirror 32 carries a dielectric coating that improves its reflectivity.

The zone of the first parabolic mirror 32 that receives the laser pulses carries a dielectric coating of the same type as that on the first mirror 30 in order to increase the reflection of these pulses. In the embodiment shown, the radii of curvature of the first parabolic mirror 32 are about 65 mm. This enables the laser pulses to be focused at a distance of 65 mm, corresponding to the front end face of the measurement endpiece 22. The diameter of the focused point of the laser pulses on the surface of the material or the article to be analyzed is about 100 micrometers (μm). This dimension is adjustable by an appropriate selection of the lenses 20 that are fitted at the outlet from the laser generator 18.

The second zone of the parabolic mirror 32, the plane mirror 52, and the second parabolic mirror 54 carry metallic coatings to improve reflection of the light that is picked up, e.g. a film having multiple dielectric layers based on aluminum in order to increase reflectivity in the visible and in the ultraviolet spectrum, e.g. in the range 190 nm to 900 nm.

The housing 10 also contains an electronic card 72 mounted under the laser generator 18 to control the generator and the various motors, safety systems, and indicators, and also a video screen 74 such as a computer terminal screen for displaying measurement results, which screen is mounted at the rear end of the housing 10 and is connected to data processor means that are housed in the unit 16 and that receive as input the signals that are output by the detectors 70.

The device operates as follows:

The housing 10 weighs about 2 kg and is held in the hand via the handle 12, while the unit 16 weighs about 3 kg to 4 kg and rests on the ground beside the operator or is fastened on the operator's back by means of a harness.

The operator presses the measurement endpiece 22 on the material or the article to be analyzed, so as to activate the safety contacts 24, and then presses on the trigger 76 in the handle in order to cause the laser generator 18 to operate with the first parabolic mirror 32 in its lowest position.

The laser generator 18 emits a series of laser pulses that are focused on a point of the surface of the material or the article to be analyzed, and by way of example the number of emitted pulses lies in the range 50 to 100 per measurement point in the example shown in the drawings. These pulses generate a plasma of vaporized material that emits light, a fraction of which is picked up through the window 28 and reflected by the first parabolic mirror 32 onto the second plane mirror 52 which returns it to the second parabolic mirror 54 in order to focus it on the inlet of the optical fiber 56 leading to the spectrometer mounted in the unit 16.

In the embodiment described and shown in the drawings, each of the linear detectors 70 comprises 2048 CCD photodetectors, each having a size of 13 µm×500 µm and receiving wavelengths in the 200 nm to 240 nm and in the 300 nm to 340 nm bands with spectral resolution of 40 picometers (µm). Integration of the electromagnetic radiation on each of the detectors is synchronized with the emission of the laser pulses, e.g. with a delay of 500 ns between laser pulse emission and the beginning of radiation integration.

The diffraction grating 66 is an etched concave grating that corrects for chromatic aberration and that has 1200 lines per millimeter, thereby giving dispersion of 2.1 nanometers per millimeter (nm/mm).

The signals output by the detectors 70 are processed by the computer means contained in the unit 16 and they are displayed on the screen 74 of the housing 10, in the form of elements forming part of the composition of the material or the article to be analyzed, together with the concentrations of these elements.

The first parabolic mirror 32 automatically calls to move in translation by pressing on the trigger 76. The first parabolic mirror 32 is moved step by step so as to scan a line that is about 1 cm long on the surface of the material or the article to be analyzed, with one measurement (corresponding to firing 50 to 100 laser pulses) being taken once every millimeter (the first ten laser pulses serving to clean the surface to some extent).

When the parabolic mirror 32 reaches the end of its stroke in the top position, the laser pulses are directed to the mirror 46 of the measurement endpiece and reflected onto the sample 50 in order to correct for any spectral drift of the spectrometer and any power drift of the laser generator, e.g. due to temperature.

The series of measurements taken on the material or the article to be analyzed serves to avoid local measurements that are falsified as a result of impurities, thereby making it possible to analyze materials that are somewhat heterogeneous, e.g. refractory materials. By using statistical processing, this also makes it possible to improve the performance of analysis.

Figure 6:
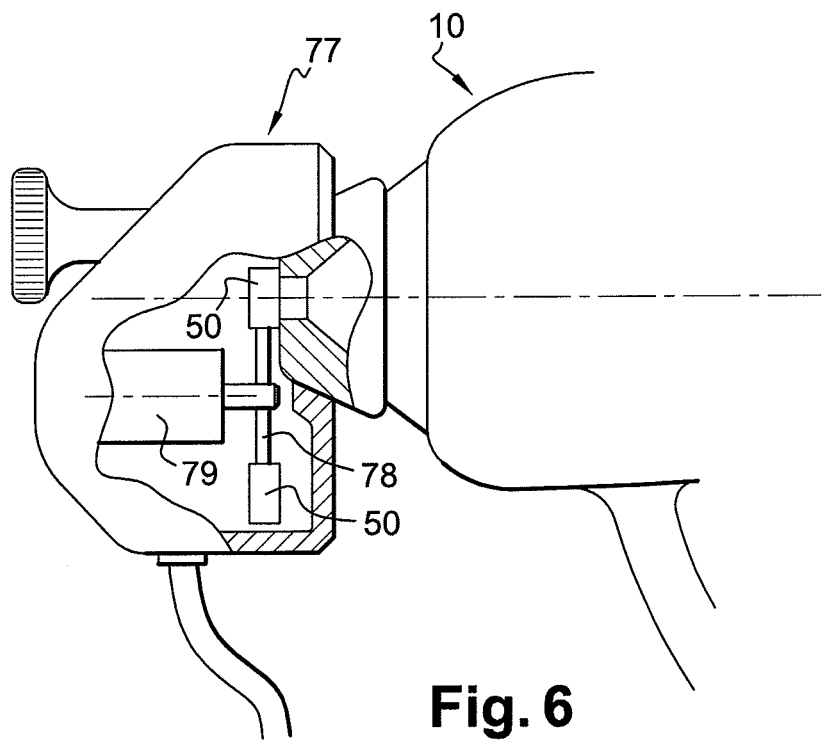
FIG. 6 is a diagram showing a calibration fitting.

Since space in the measurement endpiece is very limited, it is difficult to place more than one or two samples 50 on the sample carrier 48. In order to mitigate this drawback, the invention makes provision to mount a calibration lug 77 (see FIG. 6) on the measurement endpiece or instead of the measurement endpiece in register with the outlet window from the housing, the fitting including a motor-driven rotary disk 78 that carries about ten samples 50. The disk 78 is driven in rotation by a motor 79, e.g. powered by a universal serial bus (USB) cable, for example, with rotation of the disk 78 serving to place the various different samples on succession on the firing axis of the laser pulses.

It is thus possible to correct and verify calibration curves used for determining the concentrations of the components identified in a material or an article that has been analyzed.

It is also possible to perform automatic calibration of the analysis device, e.g. each time there is a change of application.

Figure 7:
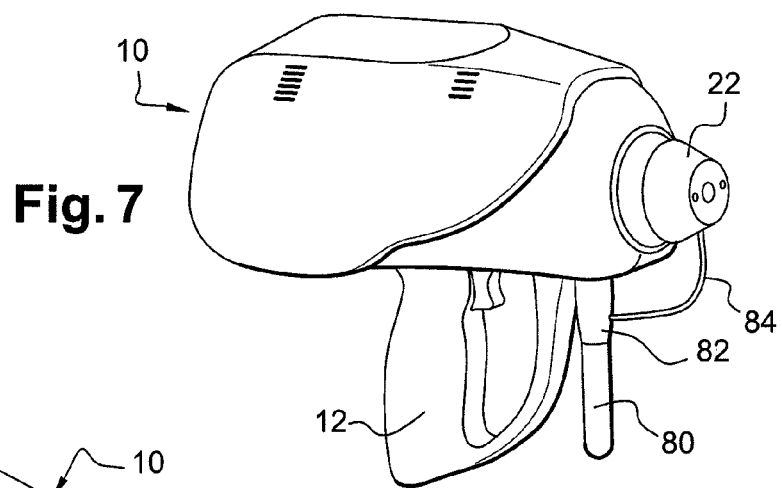
FIGS. 7, 8, and 9 are diagrammatic views of variant embodiments of the invention.

FIG. 7 is a diagram showing a variant embodiment of the invention in which the device of FIGS. 1 to 6 has an inert gas cartridge 80 added thereto, e.g. a cartridge containing argon or nitrogen, which cartridge is connected via a solenoid valve 82 and a pipe 84 to the measurement endpiece 22 in order to diffuse the inert gas in the region of the plasma formed on the surface of the material or the article to be analyzed.

The inert gas is preferably not diffused continuously, but rather intermittently, so as to limit the consumption of gas.

This makes it possible in particular to perform in situ measurements of the concentrations of elements that are normally present in ambient air, such as, for example: nitrogen, carbon, hydrogen, and oxygen. It is thus possible to measure accurately the carbon content of a steel, and to measure the concentrations of organic compounds, in particular in plastics materials. This also makes it possible to improve the repeatability of measurements by limiting the contribution of ambient air to the plasma.

According to another characteristic of the invention, the laser generator is associated with a laser diode for heating the plasma produced by a first laser pulse delivered by the laser generator 18. For this purpose, a laser diode is used that emits in the infrared, e.g. at a wavelength of 800 nm. Such a diode may deliver a pulse having a duration of 200 µs and energy lying in the range 4 mJ to 20 mJ. It is also possible to use combinations of a plurality of laser diodes ("stacks") in order to increase the total energy used for heating the plasma (e.g. in the range 20 mJ to 200 mJ).

Heating the plasma enables material to be reinjected into the plasma and to increase the temperature of the plasma. Thus, the level of the signal that is picked up is increased and the sensitivity of the measurement is improved.

Figure 8:
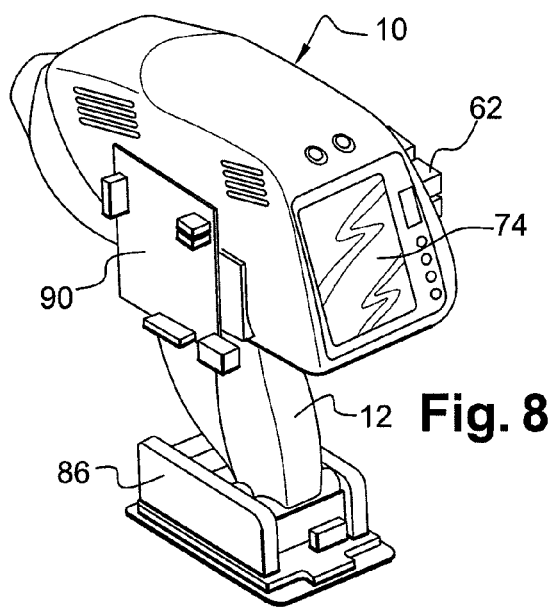

In another variant embodiment of the invention, shown diagrammatically in FIG. 8, a single house 10 is used that is both portable and self-contained and that is powered electrically from a battery 86 mounted in the bottom portion of the handle 12 of the device. The housing of the spectrometer connected to the optical fiber 56 may then be mounted on one side of the housing 10, while the control and processing card 90 is fastened on the other side of the housing 10.

The weight of the complete device of FIG. 8 is about 3.5 kg.

Figure 9:
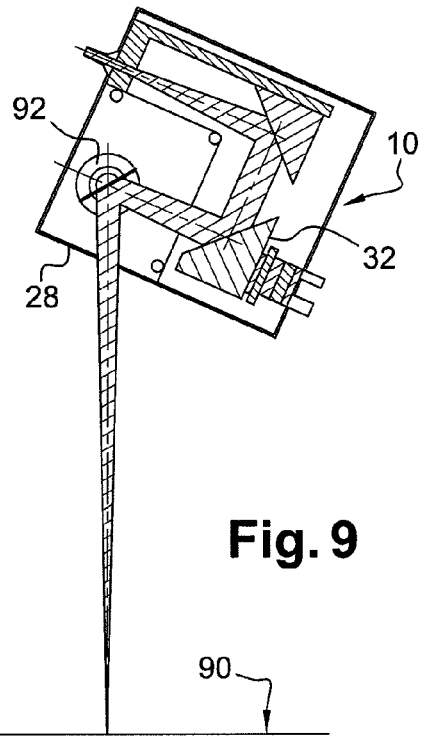

In the variant embodiment of FIG. 9 (which is a simplified view in order to facilitate understanding), the housing 10 of the device of the invention (not fitted with the endpiece 22) is mounted above a conveyor 90 in a production line, the conveyor having placed thereon materials or articles that are to be inspected or identified.

The distance between the outlet window 28 of the housing and the surface of the conveyor 90 may lie for example in the range 10 cm to 100 cm, the parabolic mirror 32 of the housing being designed to focus laser pulses on the materials or the articles that are being transported by the conveyor.

Advantageously, the housing includes a system 92 for scanning or deflecting the light beam, thus making it possible to perform measurements on articles that are not placed centrally on the conveyor.

In this variant embodiment, the housing 10 is stationary and it may be fitted with a laser generator that is more powerful.

The device of the invention has numerous and varied applications:
  analyzing and inspecting the compositions of metals, in particular of aluminum;
  analyzing and identifying plastics materials, in particular black plastics;
  analyzing and inspecting additives in plastics materials, in particular looking for banned additives and fillers;
  identifying the main ingredients of refractory parts used in industry, in particular for recycling purposes;
  detecting explosives on site; and analyzing and inspecting marking ingredients used in products of the luxury industry and of the pharmaceutical industry, in particular in the context of combating counterfeiting.

The invention claimed is:

1. A device for analyzing materials by plasma spectroscopy, the device comprising a laser generator, laser pulse focusing means for focusing laser pulses produced by the generator onto a material to be analyzed, plasma light pick-up means for picking up light from the plasma produced by the laser pulses at the surface of the material, and transmission means for transmitting said light to a spectrometer associated with photodetectors having outputs connected to data processor means, wherein the laser pulse focusing means and the plasma light pick-up means are constituted by an optical system mounted with the laser generator and laser generator control cards in a housing that is portable and suitable for handling in one hand, the optical system being mounted in the housing between the laser generator and an outlet window and comprising a first parabolic mirror for focusing the laser beam on the material to be analyzed and for picking up the light from the plasma, and two plane mirrors arranged relative to the first parabolic mirror to reflect to said mirror the laser pulses emitted by the generator and to reflect the light from the plasma as received from the first parabolic mirror to a second parabolic mirror that focuses said light on one end of the transmission means connected to the spectrometer.

2. A device according to claim 1, wherein the plane mirrors are juxtaposed and located vertically relative to the first parabolic mirror and horizontally relative to the second parabolic mirror.

3. A device according to claim 1, wherein the first parabolic mirror is movable along the axis of incidence of the laser pulses so as to scan in translation the surface of the material to be analyzed.

4. A device according to claim 3, wherein the first parabolic mirror is mounted on a support that is moved in translation by a motor-driven wormscrew controlled by the control means of the laser generator.

5. A device according to claim 3, wherein a measurement endpiece is mounted on the housing facing the outlet window and includes a calibration mirror for reflecting the laser pulses when the first parabolic mirror is in an end-of-stroke position onto a calibration sample that is mounted in the measurement endpiece.

6. A device according claim 1, wherein it includes a calibration fitting for mounting on the housing facing the outlet window, the fitting including a motor-driven support carrying a determined number of samples of different materials, the samples being placed one after another on the incidence axis of the laser pulses at the outlet from the housing.

7. A device according to claim 1, wherein the first parabolic mirror includes a laser pulse reflection zone and a plasma light reflection zone, these two zones being adjacent and separate from each other, each including a reflective coating that is adapted to the wavelengths it is to reflect.

8. A device according to claim 1, wherein the plane mirror for reflecting laser pulses has a reflective coating of the dielectric type and the plane mirror for reflecting light on the plasma includes a reflective coating of the metallic type.

9. A device according to claim 1, wherein the second parabolic mirror includes a metallic reflective coating and focuses the light from the plasma onto the end of a multimode optical fiber having its other end connected to the input of the spectrometer.

10. A device according to claim 1, wherein the spectrometer comprises a housing formed with an inlet slot fitted with a connector for coupling to the optical fiber, a diffraction grating, a mirror receiving the light diffracted by the grating, and at least one linear detector having photodetectors that receive the light reflected by said mirror.

11. A device according to claim 10, wherein the spectrometer has two substantially juxtaposed linear detectors covering distinct ranges of the light spectrum.

12. A device according to claim 11, wherein said two substantially juxtaposed linear detectors cover 200 nm to 240 nm and 300 nm to 360 nm, respectively.

13. A device according to claim 1, wherein it includes means for injecting an inert gas into the zone where plasma is formed at the surface of the material to be analyzed, said means comprising an inert gas cartridge mounted on the housing and fitted with an outlet solenoid valve connected via a pipe to the measurement endpiece.

14. A device according to claim 1, wherein it includes heater means for heating the plasma produced at the surface of the material, the heater means comprising at least one laser diode emitting pulses focused by the first parabolic mirror on the plasma formation zone.

15. A device according to claim 1, wherein the housing is connected to a unit containing a spectrometer, electrical power supply means, and a control and computer processor card.

16. A device according to claim 1, wherein the spectrometer, electrical power supply means, and a control and data processing card are carried by the housing containing the laser generator.

17. A device according to claim 1, wherein it includes means for displaying analysis results, said means comprising a computer terminal screen mounted on the rear face of the housing containing the laser generator for the purpose of displaying the ingredients of the analyzed material and the concentrations of said ingredients.

18. A device according to claim 1, wherein it is mounted in a production line, above a conveyor and at a distance therefrom, and includes means for scanning or deflecting a light beam.

19. A device according to claim 18, wherein it lies at a distance lying in the range 10 cm to 100 cm from the conveyor.

* * * * *